United States Patent [19]

Dodd, Jr. et al.

[11] Patent Number: 4,678,913

[45] Date of Patent: Jul. 7, 1987

[54] METHOD AND APPARATUS FOR ANALYZING THE NATURE OF A SAMPLE

[75] Inventors: Jack G. Dodd, Jr.; Jeffrey J. Dodd, both of Hamilton, N.Y.

[73] Assignee: Walter C. McCrone Associates, Inc., Chicago, Ill.

[21] Appl. No.: 816,262

[22] Filed: Jan. 6, 1986

[51] Int. Cl.⁴ .............................................. G01J 1/00
[52] U.S. Cl. ..................................... 250/341; 356/440
[58] Field of Search .......................... 250/338 R, 341; 356/317, 318, 440

[56] References Cited

U.S. PATENT DOCUMENTS 4,578,584  3/1986  Baumann et al. .................... 250/341

Primary Examiner—Janice A. Howell
Attorney, Agent, or Firm—Lee, Smith & Zickert

[57] ABSTRACT

A method and apparatus for analyzing the absorption spectra of a minute sample. The sample is placed in a hollow enclosure which is sealed after a suitable working fluid is introduced into the enclosure. When a vapor equilibrium is reached within the enclosure creating a droplet condensate of working fluid about the sample, the sample is first irradiated with dark-field visible illumination with an image thereof stored, and is then irradiated with infrared radiation and a second dark-field image stored. The stored images are analyzed and the procedure is repeated for a plurality of different frequencies spanning the range of infrared absorption of the sample.

20 Claims, 1 Drawing Figure

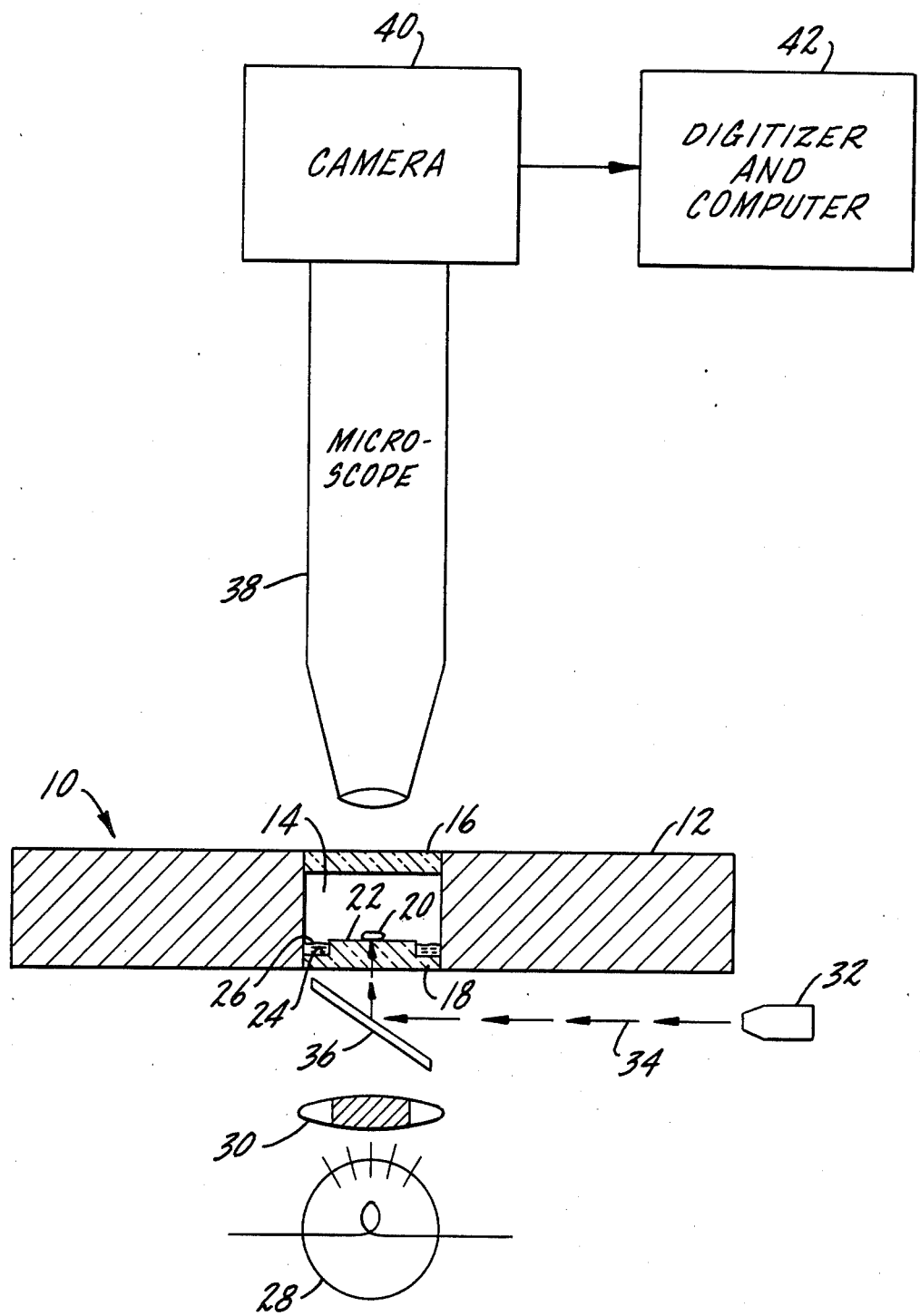

METHOD AND APPARATUS FOR ANALYZING THE NATURE OF A SAMPLE

BACKGROUND OF THE INVENTION

This invention relates to determining the nature of a minute particle or sample through infrared detection techniques, and in particular to a method and apparatus for determining the nature of the sample by heating the sample over a range of infrared frequencies and measuring the resultant infrared absorption of the sample.

There are known methods for determining the molecular characterization, and therefore nature, of small samples of matter. Standard infrared spectrometric methods have been well know for quite some time, but are not readily useable for very small particles, and therefore not available for determining the molecular nature, as opposed to the elemental nature, of a particle. Other methods of spectrometry, such as the Raman method, are known and used to determine the characteristics of particles as small as 10 microns, with difficulty at that small size. The Raman method suffers the deficiency that the number of reference spectra for the Raman method is not nearly as large as the number of reference spectra available when using standard infrared spectrometric methods. In addition, when using the Raman method, large amounts of energy are employed. When organic samples are studied, the Raman method cannot be employed since live cells would be destroyed.

SUMMARY OF THE INVENTION

The invention pertains to a method and apparatus for analyzing the absorption spectra of a minute sample which avoids the detracting features of the prior art, the spectra obtained from the invention can be compared with the large number of available infrared reference spectra in order to determine the molecular characterization of the sample studied.

The apparatus includes a container for retaining the sample, with the container comprising a carrier, a sealed, hollow sample enclosure formed in the carrier, means forming a transparent path through the enclosure with the path being transparent to both infrared and visible radiation, and a working fluid disposed within the enclosure, the working fluid also being transparent to infrared radiation. A source of tunable infrared radiation is oriented to pass infrared radiation through the enclosure along the transparent path. A visible light source is positioned to pass visible radiation through the enclosure. An image of the sample within the enclosure is then captured and stored.

The stored image is also analyzed. The image is converted in a digitizer to a computer-readable format and a computer is then used for examining the converted image. In accordance with the preferred embodiment of the invention, the computer is used to analyze an image of the sample when first irradiated only by visible radiation, and then when subsequently irradiated also by infrared radiation.

In accordance with the illustrated embodiment of the invention, the container includes a raised sample platform formed in the enclosure and a well formed about the platform, with the working fluid being located in the well. Preferably, the well is annular.

For capturing and storing an image of the sample, preferably a dark-field light microscope and a camera are employed. A dark-field condenser is used to produce dark-field illumination.

The transparent path is comprised of first and second windows on opposite sides of the enclosure of the sample container. The windows, in combination with the carrier, form a hollow cell for containing the sample. One of the windows also serves as the sample platform for the sample.

The working fluid comprises an infrared transparent liquid. Suitable liquids have been determined to be pentane, liquid argon and water, the latter when analyzing organic matters.

To analyze the sample, the sample is first located in the hollow enclosure. The working fluid is then introduced into the enclosure without directly contacting the sample, and the enclosure is then sealed to create a vapor equilibrium within the enclosure. When the equilibrium has been reached, a droplet condensate of the working fluid is created about the sample. The sample is then irradiated with radiation, the size of the droplet is detected and stored, and the procedure of irradiating, detecting and storing is repeated for a plurality of frequencies spanning the range of infrared absoption of the sample.

BRIEF DESCRIPTION OF THE DRAWING

The invention is described in greater detail in the following description of examples embodying the best mode of the invention, taken in conjunction with the single drawing FIGURE, in which is illustrated an apparatus according to the invention for determining the absorption spectra of a sample using dark-field infrared procedures according to the invention.

DESCRIPTION OF EXAMPLES EMBODYING THE BEST MODE OF THE INVENTION

The apparatus of the invention is depicted schematically in the single drawing FIGURE. The depiction of the apparatus is not intended to be to scale and parts are exaggerated in size and shown schematically for the purposes of description.

For retaining the sample, a container 10 is employed. The container 10 includes a carrier 12 which is shaped for mounting in a stationary orientation. Thus, the carrier 12 is shown in the rectangular form of a common slide for microscopic examination.

The carrier 12 includes a sealed, hollow sample enclosure 14 formed centrally therein. A transparent path is formed through the enclosure 14 by means of top and bottom windows 16 and 18, respectively, which are formed of a material which is transparent to both infrared and visible radiation. A sample 20 to be analyzed is situated within the enclosure 14. Since the invention is intended for analysis of particles of very small size, the sample 20 will normally be a particle of 10 microns or less in diameter.

The window 18 is shaped to form a raised sample platform 22 for the sample 20. A well 24, preferably annular, is formed in the window 18 about the platform 22 and a suitable working fluid 26 is disposed within the well 24 about the sample 20.

A visible light source 28 is oriented beneath the container 10. In order to permit conversion to dark-field illumination, a dark-field condenser 30 is interposed between the light source 28 and the container 10.

Infrared radiation is provided by an infrared radiator or source 32, emitting an infrared beam 34 as illustrated which is reflected by a beam splitter 36 to pass through the sample 20. As is conventional, the beam splitter 36 is transparent to dark-field light from the combination of the light source 28 and dark-field condensor 30.

A dark-field microscope 38 is employed to capture an image of the irradiated sample 20. The image is recorded by a camera 40. For analysis purposes, in accordance with the preferred procedure of the invention, the recorded image from the camera 40 is digitized and stored in a downstream combination of a digitizer and computer 42. In the computer, the image may then be studied further.

The working fluid 26 must be compatible with the sample 20 to be analyzed. The fluid 26 must not dissolve or react with the sample, must have a suitable working temperature range, and must be transparent to infrared radiation in the region of spectral interest. The applicants have found that, for non-soluble substances, pentane is an appropriate working fluid for working at room temperature, and has wide ranges of infrared transparency. Also, by proper design to accomodate the temperatures involved, liquid argon may also be used. Liquid argon has almost complete infrared transparency, and is entirely non-reactive. Finally, for analysis of biological materials such as single cells, water must be used as the working fluid. While water has extensive infrared absorption bands, these absorption bands duplicate those present in a cell due to the water it contains, and therefore do not interfere with observation. Because water must be used at biologically compatible temperatures, an appropriate desired vapor/liquid equilibrium state within the sample enclosure 14 must be established by increasing the pressure within the enclosure 14 by various pumping methods.

In operation, the sample to be anlyzed is placed in the enclosure 14 on the sample platform 22. The working fluid 26 is introduced into the annular well 24 and the enclosure 14 is closed and sealed by the window 16. An equilibrium vapor pressure is established within the enclosure 14, and working fluid 26 condenses about and forms a droplet around the sample 20. The droplet, which is not illustrated in the drawing, is tightly bonded to the sample 20 by surface tension, and the size of the droplet depends upon establishment of a vapor/liquid equilibrium within the enclosure 14, and therefore upon the temperature within the enclosure 14. It has been found that the size of the droplet ranges from about twice the size of the sample 29 for particles 10 microns in diameter to many times the particle diameter for smaller particles. Under the dark-field illumination method of the invention, the brightness of the droplets makes their observation quite simple.

As is well known, the total light scattered by a droplet is a function of the diameter of the droplet. Therefore, an increase in the temperature of the particle due to infrared heating will result in a decrease in the size of the droplet. Consequently, the light scattered by the droplet will decrease as the droplet assumes a new, smaller equilibrium size. Thus, the temperature of the particle can be accurately monitored by monitoring the total light scattered by the droplet surrounding the sample 20.

The infrared beam 34 striking the sample 20 heats the sample at those wavelengths where the sample absorbs the infrared radiation. By tuning the infrared beam 34 and source 32 through the region of spectral interest, the infrared absorption spectrum of the sample 20 may be determined and stored by the computer 42.

It therefore is practical to determine the absorption spectrum of any particle that will serve as a nucleus for a condensation droplet visible in the dark-field microscope 38. It has been determined that particles as small a 2 or 3 microns can easily be analyzed by the method and apparatus of the invention using an infrared source 32 which can deliver intensities of about 1 watt per square centimeter. Such intensities are available from commercial monochromators of from Fourier transform infrared illuminators. For test purposes any other appropriate source can be substituted for the infrared source 32, so long as the source can simulate an infrared source. A low-power helium-neonlaser has been utilized with success.

Two images of the sample 20 are taken for each different frequency of the infrared source 32. The first is of the sample 20 when illuminated by dark-field light but without being irradiated by the infrared beam 34. After that image is captured, the source 32 is activated and, after equilibrium within the enclosure 14 is again established, a second dark-field image is captured in the camera 40. The process is repeated for each desired frequency from the infrared source 32.

In the digitizer and computer 42, the two images for each infrared frequency are first digitized, and then the image obtained after heating by the infrared beam 34 is subtracted from the image without heating. The resultant data is stored in the computer for each frequency, and following accumulation of data throughout the desired spectral range, the nature of the sample 20 can then readily be determined using the spectral information obtained.

Various changes to the invention can be made without departing from the spirit thereof or scope of the following claims.

What is claimed is:

1. An apparatus for analyzing the absorption spectra of a sample, comprising
    a. a container for retaining the sample, said container including
        i. a carrier,
        ii. a sealed, hollow sample enclosure formed in the carrier,
        iii. means forming a transparent path through said enclosure, said path being transparent to both infrared and visible radiation,
        iv. a working fluid disposed within said enclosure, said fluid being transparent to infrared radiation,
    b. a source of tunable infrared radiation oriented to pass infrared radiation through said enclosure along said path,
    c. a visible light source oriented to pass visible radiation through said enclosure, and
    d. means for capturing and storing an image of a sample within said enclosure.

2. An apparatus according to claim 1 including means for analyzing a stored image of a sample.

3. An apparatus according to claim 2 in which said analyzing means comprises a digitizer for converting said stored image into a computer-readable format and a computer for examining said converted image.

4. An apparatus according to claim 1 including a raised sample platform formed in said enclosure and a well formed in said enclosure about said platform, said working fluid being located in said well.

5. An apparatus according to claim 4 in which said well is annular.

6. An apparatus according to claim 1 in which said means for capturing and storing comprises a dark-field light microscope and a camera.

7. An apparatus according to claim 1 including a dark-field condenser disposed between said visible light source and said cell.

8. An apparatus according to claim 1 in which said means forming a transparent path comprises a first window located at one side of said enclosure and a second window, spaced from the first window, located at an opposite side of said enclosure, said spaced windows, in combination with said carrier, forming a cell for the sample.

9. An apparatus according to claim 1 in which said working fluid comprises an infrared transparent liquid.

10. An apparatus according to claim 9 in which said working fluid is selected from the group comprising pentane, liquid argon and water.

11. A container for retaining a sample for analysis of the absorption spectra of the sample, comprising
   a. a carrier shaped for mounting in a stationary orientation,
   b. a sealed, hollow sample enclosure formed in the carrier,
   c. means forming a transparent path through said enclosure, said path being transparent to both infrared and visible radiation, and
   d. a working fluid disposed within said enclosure, said fluid being transparent to infrared radiation.

12. A container according to claim 11 including a raised sample platform formed in said enclosure and a well formed in said enclosure about said platform, said working fluid being located in said well.

13. A container according to claim 12 in which said well is annular.

14. A container according to claim 11 in which said means forming a transparent path comprises a first window located at one side of said enclosure and a second window, spaced from the first window, located at an opposite side of said enclosure, said spaced windows, in combination with said carrier, forming a cell for the sample.

15. A container according to claim 11 in which said working fluid comprises an infrared transparent liquid.

16. A container according to claim 15 in which said working fluid is selected from the group comprising pentane, liquid argon and water.

17. A method of determining the absorption spectra of a sample, comprising the steps of
   a. locating the sample in a hollow enclosure,
   b. introducing a working fluid into said enclosure out of direct contact with the sample,
   c. sealing said enclosure such that a vapor equilibrium is reached within said enclosure creating a droplet condensate of said working fluid about said sample,
   d. irradiating said sample with infrared radiation of a given frequency,
   e. detecting the size of said droplet,
   f. storing a representation indicative of the detected size of said droplet,
   g. repeating steps "d" through "f" for a plurality of given frequencies spanning the range of infrared absorption of the sample.

18. The method according to claim 17 in which method step "d" includes the step of irradiating said sample with visible radiation prior to irradiation with infrared radiation, method step "e" includes detecting the size of said droplet both when irradiated with visible radiation and when irradiated with infrared radiation, and method step "f" includes storing a first respresentation of the detected size of said droplet when irradiated with visible radiation and a second representation when irradiated with infrared radiation.

19. The method according to claim 18 including the step, following step "f", of analyzing the stored images.

20. The method according to claim 19 in which the analyzing step includes the steps of digitizing each said respresentation, subtracting the digitized second representation from the corresponding digitized first respresentation, and storing the resulting subtracted representation for further examination.

* * * * *